United States Patent [19]

Murtha et al.

[11] 4,178,269

[45] Dec. 11, 1979

[54] HYDROALKYLATION COMPOSITION AND PROCESS FOR PRODUCING SAID COMPOSITION

[75] Inventors: Timothy P. Murtha; Ernest A. Zuech, both of Bartlesville, Okla.

[73] Assignee: Phillips Petroleum Company, Bartlesville, Okla.

[21] Appl. No.: 866,135

[22] Filed: Dec. 30, 1977

Related U.S. Application Data

[62] Division of Ser. No. 766,640, Feb. 8, 1977, Pat. No. 4,094,920.

[51] Int. Cl.$^2$ .......................... B01J 27/06; B01J 29/06
[52] U.S. Cl. ................................. 252/441; 252/455 Z
[58] Field of Search ............................ 252/455 Z, 441

[56] References Cited

U.S. PATENT DOCUMENTS

| | | | |
|---|---|---|---|
| 3,173,854 | 3/1965 | Eastwood et al. | 252/455 Z |
| 3,534,115 | 10/1970 | Bushick | 252/455 Z |
| 3,546,100 | 12/1970 | Yan | 252/455 Z |
| 3,691,255 | 9/1972 | Takase et al. | 252/455 Z |
| 3,783,123 | 1/1974 | Young | 252/455 Z |
| 3,867,307 | 2/1975 | Scherzer et al. | 252/455 Z |

*Primary Examiner*—Carl Dees

[57] ABSTRACT

An aromatic hydrocarbon is contacted under hydroalkylation conditions and in the presence of hydrogen with a composition comprising at least one platinum compound supported on a calcined, acidic, nickel and rare earth-treated crystalline zeolite which additionally has a halide content sufficient to promote the selectivity of the composition to produce a desired cycloalkyl aromatic hydrocarbon.

16 Claims, No Drawings

HYDROALKYLATION COMPOSITION AND PROCESS FOR PRODUCING SAID COMPOSITION

This is a division of application Ser. No. 766,640, filed Feb. 8, 1977, now U.S. Pat. No. 4,094,920.

The invention relates to a hydroalkylation process, a composition useful as a catalyst in said process and a method for producing said composition.

Prior art catalysts in the field of hydroalkylation processes suffered from several drawbacks. These deficiencies of the prior art catalysts for the hydroalkylation reaction included: (1) The use of support materials for certain catalysts which are not able to withstand the temperatures employed in a typical air burn-off regeneration operation. Such regeneration operations are commonplace in the catalytic art for hydrocarbon conversions of various types and it is highly desirable that the catalyst for the hydroalkylation process be stable to such typically employed regeneration conditions. (2) In the hydroalkylation of aromatic hydrocarbons to cycloalkyl aromatic hydrocarbons, a problem in terms of selectivity to the desired product is often evident. For example, in the conversion of benzene to cyclohexylbenzene, by-products such as cyclohexane and methylcyclopentylbenzene as well as dicyclohexylbenzene and other heavier molecules can often be produced in such quantities that the process can become uneconomical. Thus, a more selective hydroalkylation catalyst is desired with little or no decrease in catalyst activity. It is, however, recognized that a decrease in catalyst activity can often be tolerated if there is a concomitant increase in selectivity to the desired product. (3) A number of the catalysts of the prior art for the hydroalkylation reaction are prepared by very complex and time consuming processes. For example, starting with a powdered crystalline zeolite support, said support is cation exchanged, washed and then incorporated into a matrix of another material such as silica-alumina. This combination is calcined, cooled, and impregnated with certain metal salts. Finally the composite is extruded into pellets and the like. Thus, it is desirable that a more simplified and less expensive process for making active and selective catalysts be found. (4) Certain catalysts of the prior art for the hydroalkylation reaction were of fixed acidity because of the type of support material utilized. This left little variation that could be made in this important property of the hydroalkylation catalyst. It is therefore desirable that catalysts be developed which are varied easily in their acidity characteristics.

It is an object of the present invention to hydroalkylate aromatic compounds.

Another object of the present invention is to provide a method for producing a composition useful as a hydroalkylation catalyst.

Another object of the invention is a composition useful as a catalyst in hydroalkylation reactions which is regenerated by air burn-off.

Another object of the invention is a composition useful as a catalyst in hydroalkylation reactions which is more active and more selective than prior art catalysts.

Another object of the invention is a composition useful as a catalyst in hydroalkylation reactions which is simpler and less expensive to produce as compared to prior art catalysts.

Still another object of the invention is a composition useful as a catalyst in hydroalkylation reactions in which the acidity of the catalyst can be adjusted.

SUMMARY

According to the invention an aromatic hydrocarbon is contacted under hydroalkylation conditions and in the presence of hydrogen with a composition comprising at least one platinum compound supported on a nickel and rare earth-treated crystalline zeolite support which is calcined to produce an acidic support before or after impregnating the platinum compound on the support wherein said composition further comprises a halide content sufficient to promote the selectivity of the composition to produce a desired cycloalkyl aromatic hydrocarbon. Such a composition when used as a catalyst is regenerated by air burn-off and is a highly active and selective catalyst.

Further according to the invention an aromatic hydrocarbon is contacted under hydroalkylation conditions and in the presence of hydrogen with a composition comprising at least one platinum compound supported on a nickel and rare earth-treated crystalline zeolite support which is calcined to produce an acidic support before or after impregnating the platinum compound on the support wherein said composition further comprises a halide content ranging from about 0.1 to about 100 milligrams of elemental halogen per gram of the composition.

Further according to the invention a composition comprises at least one platinum compound supported on a calcined, acidic, nickel and rare earth-treated crystalline zeolite which additionally has a halide content ranging from about 0.1 to about 100 milligrams of elemental halogen per gram of the composition.

Further according to the invention the above composition is prepared by contacting a crystalline zeolite with an aqueous cation exchange solution comprising rare earth, nickel and ammonium compounds; removing the zeolite from said solution and washing said zeolite with water to remove excess ions; calcining said cation exchange zeolite; cooling said calcined zeolite; impregnating said cation exchange zeolite before or after said calcination step with a solution comprising at least one platinum compound in a suitable solvent and removing said solvent by evaporation and subsequently contacting said platinum impregnated and calcined zeolite with a halogen containing compound in an amount ranging from about 0.1 to about 100 milligrams of elemental halogen per gram of the composition.

Further according to the invention a composition comprises at least one platinum compound supported on a calcined, acidic, nickel and rare earth-treated crystalline zeolite which additionally has a halide content sufficient to promote the selectivity of the composition to produce a desired cycloalkyl aromatic hydrocarbon when used to contact an aromatic hydrocarbon in a hydroalkylation reaction.

Further according to the invention the above composition is prepared by contacting a crystalline zeolite with an aqueous cation exchange solution comprising rare earth, nickel and ammonium compounds; removing the zeolite from said solution and washing said zeolite with water to remove excess ions; calcining said cation exchanged zeolite; cooling said calcined zeolite; impregnating said cation exchanged zeolite before or after said calcination step with a solution comprising at least one platinum compound in a suitable solvent and removing said solvent by evaporation and subsequently contacting said platinum impregnated and calcined zeolite with a halogen-containing compound in an amount sufficient to promote the selectivity of said composition to produce a desired cycloalkyl aromatic hydrocarbon when said composition is used to contact an aromatic hydrocarbon in a hydroalkylation process. The acidity of the above composition is easily adjusted by varying the conditions under which the cation exchange step is carried out, such as, for example, adjusting the concentration of an ammonium compound in the cation exchange solution.

DETAILED DESCRIPTION OF THE INVENTION

The composition of the instant invention can be briefly described as a platinum impregnated crystalline zeolite which has been cation exchanged with rare earth, nickel and ammonium compounds, calcined either before or after the platinum impregnation step and followed by contacting the platinum impregnated zeolite with a halogen-containing compound. It was discovered that the presence of the halide in a relatively small amount as compared to the total weight of the catalyst significantly increases the selectivity of the catalyst to produce a cycloalkyl aromatic hydrocarbon when the catalyst is used to hydroalkylate aromatic hydrocarbons as compared to the same catalyst without the halide component. Generally the presence of the halide component reduces the activity of the catalyst somewhat, but generally the increase in selectivity more than compensates for the reduction in activity. Although not absolutely necessary, it is preferred that the above catalyst be treated with hydrogen prior to introduction of the aromatic hydrocarbon feed in the hydroalkylation process because of improved results.

The compositions of the instant invention are useful as catalysts and to some extent solve or obviate each of the above-mentioned deficiencies of the prior art catalyst. For example, the supports utilized for the compositions of the instant invention are stable to regeneration conditions utilized under typical air burn-off operations; they appear to operate at higher levels of productivity in that they show a higher degree of activity and selectivity than certain of the prior art catalysts; the process of making the compositions of the instant invention is simple and straightforward and the compositions thus obtained should be less expensive than those of the prior art which utilize very complex steps in their preparation; and the compositions of the instant invention can be made with a high degree of flexibility in the degree of acidity simply by adjusting the cation exchange conditions on the crystalline zeolite support utilized for the compositions of this invention.

The support material for the composition employed in the instant invention is a crystalline zeolite which has been treated under cation exchange conditions with rare earth, nickel and ammonium compounds such that the cation metal content of the support is partially exchanged. Generally the cationic metal is an alkali metal which is sufficiently removed by cation exchange such that the remaining alkali metal content after the cation exchange step ranges from about 0.01 to about 2 percent by weight; however, the runs carried out in accordance with the invention and reported herein indicate that good results can be obtained when the alkali metal content of the cation exchanged zeolite ranges from about 0.1 to about 1 percent by weight. Some of the more commonly employed crystalline zeolites which are suitable for use in accordance with the present invention are the Type X or Type Y crystalline zeolites which are sometimes called molecular sieves because of their essentially uniform pore diameters. Some suitable Type Y synthetic crystalline zeolites are described for example in U.S. Pat. No. 3,130,007 and some suitable Type X zeolites are described in U.S. Pat. No. 2,882,244. Such materials are presently commercially available as for example zeolites SK-40 (Type Y) and 13X (Type X) from the Linde Division of Union Carbide Corporation, New York, New York.

The alkali metal form of the crystalline zeolites usually comprises sodium as the alkali metal and said zeolites are treated under cation exchange conditions with a mixture of rare earth, nickel and ammonium compounds in accordance with the present invention in order to provide a suitable support material for use in the preparation of the compositions of the invention.

It is contemplated that any of the readily available rare earth metal compounds may be employed in the cation exchange solution. Generally, the compounds used are those in which the rare earth metal-containing ion is present in the cationic state. Representative rare earth metal compounds include nitrates, bromides, acetates, chlorides, iodides, sulfates and mixtures thereof of one or more of the rare earth metals including cerium, lanthanum, praseodymium, neodymium, samarium, europium, gadolinium, terbium, dysprosium, holmium, erbium, thulium, ytterbium, and lutetium. Compounds of the rare earths named above may be employed singly, however, it is often convenient to employ commercially available mixtures of the rare earths. For example, mixtures of rare earth metal compounds such as the chlorides of lanthanum, cerium, praseodymium, neodymium, samarium, and gadolinium are available commercially at a relatively low cost and may be effectively employed.

As noted above, the zeolite material is cation exchanged with a mixture of rare earth, nickel and ammonium compounds according to the instant invention. Any convenient ammonium compound may be employed although the chloride is preferred because it is inexpensive and readily available. The weight ratio of ammonium compound to nickel and rare earth compounds in the aqueous exchange solution can be selected over a broad range. Generally the weight ratio of ammonium compound to nickel and rare earth compounds combined is within the range of from about 0.5:1 to about 20:1, although the data contained herein indicates that a range of from about 0.2:1 to about 5:1 can be used with good results. The concentration of rare earth compounds in the aqueous exchange solution can be varied over a wide range and exchange conditions can be adjusted accordingly such that the rare earth content of the ion exchanged crystalline zeolite can be selected over a broad range. Generally, the content of the final catalyst composite in terms of the rare earth elements is from about 2 to about 25 weight percent. The runs described herein indicate that the rare earth content of the catalyst can be within the range of from 5 to 20 weight percent. Good results were obtained employing a rare earth content of about 10 percent by weight. As noted above, the alkali metal content, for example sodium, of the exchanged catalyst support is partially removed by the ion exchange step and the alkali metal is generally from about 0.01 to about 2 percent by weight; however, the runs described herein indicate that good results can be obtained employing an alkali metal content ranging from about 0.1 to about 1 percent by weight.

The nickel compounds which will be employed in admixture with the above-named rare earth metal compounds and ammonium compounds are those wherein the nickel ion is present in the cationic state. Some suitable compounds representative of the nickel compounds which can be used in the invention include the nitrates, bromides, acetates, chlorides, iodides, sulfates and mixtures thereof.

The nickel content in the final composition can also be selected over a broad range. Generally the composition will comprise from about 0.01 to about 15 weight percent nickel, although the runs carried out in accordance with the invention and described herein indicate that good results can be obtained employing a nickel content ranging from about 1 to about 8 percent by weight of said composition.

The procedure whereby the Type X and Type Y zeolites are treated with aqueous solutions of rare earth, nickel and ammonium compounds to replace a portion of the alkali metal content of the zeolite is a cation exchange process which can be carried out in a batch or continuous fashion. Generally the exchange process is carried out on a continuous basis under the following typical conditions. A fixed bed of the zeolite material is treated with said aqueous solution of the rare earth, nickel and ammonium compounds at a temperature of 90° to 110° C. under conditions such that from about 0.1 to about 0.5 of the volume of aqueous salts solution per volume of zeolite is in contact with said zeolite per hour or, in other words, an LHSV ranging from about 0.1 to about 0.5 is employed in the exchange process. Under these conditions, the exchange process can be completed in 48 hours or less to achieve the desired level of rare earth, nickel and ammonium ions in the zeolite. The exchanged zeolite is then washed free of excess ions from the exchange step with water. The excess wash water is removed by drying the zeolite at a temperature ranging from about 100° C. to about 300° C. just prior to calcination. The instant catalyst can be calcined before impregnation with the platinum compound to be described below or the impregnation can be carried out prior to the calcination step. In either case, the calcination is carried out by slowly heating the zeolite from about 100° to 200° C. to a temperature within the range of from about 200° to about 550° C. in order to calcine the zeolite and convert the ammonium cations to the hydrogen form. Usually, the calcination is conducted until a constant weight is obtained for the zeolitic material, generally from about 2 to about 10 hours. The calcined zeolite is then cooled in ambient air, i.e., under conditions of normal humidity.

The above-described support is impregnated with a solution of at least one platinum compound followed by evaporation of the solvent used in the impregnation step. Evaporation of the solvent can be conducted under vacuum if desired. Suitable solvents include water, alcohols, such as ethanol, ketones, such as acetone, and the like. Some of the various platinum compounds that can be employed in the impregnation step are as follows: ammonium hexachloroplatinate(IV), ammonium tetrachloroplatinate(II), chloroplatinic acid, diaminoplatinum dinitrite, platinic acid, platinum tetrachloride and mixtures thereof. The impregnation is generally carried out under what may be called "total impregnation" whereby the entire solids in the solutions used in the impregnation are left on the catalyst support and the liquid solvent for said compounds is simply removed by evaporation.

The platinum content in the final composition can be selected over a broad range. Generally the platinum content ranges from 0.01 to about 1 percent by weight of said composition although the runs described herein indicate that good results can be obtained employing a platinum content within the range of from about 0.05 to 0.25 percent by weight of said composition.

The halogen-containing compounds which can be utilized according to the instant invention as a source of halide include the elemental halogens themselves such as fluorine, bromine, chlorine or iodine and the hydrohalides of said elements (HF, HBr, HCl and HI). Use of the above compounds generally requires careful control of the addition, and it is preferred to employ organic compounds which contain halogen in the instant invention. A wide variety of halogen-containing organic compounds can be employed to provide the necessary halide for use in the instant invention. These compounds can contain one or more atoms of fluorine, bromine, chlorine or iodine or mixtures thereof per molecule and the carbon content of such compounds is generally in the range of from 1 to 4 carbon atoms per molecule. For example, such compounds include alkyl halides, acid halides, or fully halogenated carbon compounds such as carbon tetrachloride or tetrachloroethylene and the like. Examples of other suitable organic compounds which can be employed include chloroform, bromoform, dichloromethane, dibromomethane, difluoromethane, chloromethane, bromomethane, 1,4-dichlorobutane, 1,4-dibromobutane, 1-chlorobutane, 1-fluorobutane, 1-bromobutane, 1,2-dichloroethane, 1,2-dibromoethane, 2-chloropropane, 2-bromopropane, acetyl chloride, acetyl iodide, acetyl bromide, bromochloromethane, 1-bromo-4-chlorobutane, 1,2-dichloroethylene, 1,2-dibromoethylene and mixtures thereof. From the results of the runs disclosed herein, it is believed that organic compounds containing chlorine or bromine will produce the best results and thus such compounds are preferred.

The hydroalkylation catalysts are modified with a halide source compound according to the instant invention by simply adding said halide source compound to the catalyst prior to or simultaneous with contacting the aromatic hydrocarbon feed in the hydroalkylation process. Because such small amounts of the halide source compound are employed, one method for adding the halide source compound to the catalyst which has been very satisfactory is to dilute the halide source compound with the aromatic hydrocarbon feed and thus contact the catalyst with the feed simultaneously with the halide source compound. It is presently believed that the halogen component of the catalyst which has been treated with the halide source compound exists in the halide form and thus is referred to herein as a halide, but the exact form of the halogen component of the catalyst has not been investigated and is not to be a limitation on the invention.

The amount of the halide added per gram of catalyst utilized is an important aspect of the present invention because too much halide will poison the catalyst whereas too little halide will not improve the selectivity of the catalyst to the desired cycloalkyl aromatic hydrocarbon. Thus, the halide content of the composition is that amount sufficient to improve the selectivity of the composition to the desired cycloalkyl aromatic hydrocarbon. Generally, the amount of halide added to the catalyst ranges from about 0.1 to about 100 milligrams of elemental halogen per gram of catalyst; however, based upon the results of the runs described herein, it is expected that the amount of halide added to the catalyst will more often range from about 0.5 to about 10 milligrams of elemental halogen per gram of catalyst.

The addition of the halide source compounds to the aromatic hydrocarbon feed stream can be utilized when the catalyst is fresh, i.e., previously unused, or can also be utilized after one or more regenerations of the above-mentioned catalyst. As most of the runs described herein indicate, a fresh catalyst is improved somewhat by regeneration and in many cases it may be desirable to subject a fresh catalyst to the regeneration process prior to using it. A typical regeneration procedure for the above-described catalyst includes purging the system of hydrogen with an inert gas such as nitrogen, then allowing air to enter the reaction zone and heating to a range of 400°–500° C. in the presence of flowing air and maintaining this temperature in the presence of flowing air for a total time of about three hours. The catalyst is then cooled in the presence of flowing air or nitrogen and at a temperature of about 200° C. is reduced with hydrogen for a period of about 0.5 to 1 hour. The catalyst is then cooled to the desired reaction temperature and is then ready for use in the hydroalkylation reaction. Generally, it is desirable to retreat the catalyst with the halogen-containing compound after each regeneration process to insure that the catalyst will provide the highest selectivity to the desired cycloalkyl aromatic compound.

Although the compound or compounds which serve as the source of halide to modify the hydroalkylation catalyst of this invention can be added to the hydrocarbon feed in one portion, good results were obtained by adding the halogen-containing compound to the feed over a period of time, generally from about 1 to about 3 hours although longer times can and were employed. It is believed that a more efficient utilization of the halide source compound is achieved by the above-described gradual addition of said compounds to the catalyst, such as when that halide source compound is added to the hydrocarbon feed, but in some instances a shorter catalyst modification time may be more desirable and produce an equal or superior catalyst.

The composition described above is employed for the hydroalkylation of aromatic hydrocarbons to produce cycloalkyl aromatic hydrocarbons. Some of the feedstocks which are suitable for use in the present invention are aromatic compounds, i.e., monocyclic aromatic hydrocarbons and alkyl-substituted monocyclic aromatic hydrocarbons. Some specific examples of these are benzene, toluene, xylene, and the like, and mixtures thereof. The aromatic hydrocarbon feedstocks should be essentially free of sulfur-containing compounds and other known poisons for hydrogenation catalysts in general. However, it is believed that a small amount of water, e.g., 5 to 100 ppm, in the feedstock is beneficial for maintaining catalyst activity over an extended period, e.g., several days.

The invention is particularly valuable for the conversion of benzene to cyclohexylbenzene. Cyclohexylbenzene is known as a valuable solvent and chemical intermediate. It can be converted in high yield to phenol and cyclohexanone by autooxidation with subsequent acid treatment. It is also useful as an intermediate in the production of cyclohexene which in turn can be utilized for the production of adipic acid and caprolactam.

The aromatic hydrocarbon feedstock is fed to the catalyst in a reaction zone operated under a wide range of conditions. The feedstock liquid hourly space velocity (LHSV), reaction temperature and pressure, and the hydrogen feed rate are not particularly critical; however, the liquid hourly space velocity (LHSV) generally ranges from about 1 to about 100, the reaction pressure generally ranges from about 690 to about 13,800 kPa (about 100 to about 2,000 psig), the hydrogen feed rate generally ranging from about 0.2 to about 1 mole per mole of aromatic hydrocarbon feedstock per hour, and the reaction temperature generally ranging from about 100° to about 250° C. Based upon the runs described herein good results can be obtained employing a liquid hourly space velocity (LHSV) within the range of from about 5 to about 30, a reaction pressure within the range of from about 1,380 to about 6,900 kPa (about 200 to about 1,000 psig), the hydrogen feed rate within the range of from about 0.2 to about 1 mole per mole of aromatic hydrocarbon feed per hour, and the reaction temperature within the range of from about 140° to about 200° C.

The hydroalkylation reaction is conveniently carried out by having the above-described catalyst is a fixed bed reactor and then contacting said catalyst with the aromatic hydrocarbon feed and hydrogen in an upflow or downflow arrangement. It is also possible to employ a countercurrent flow of hydrogen and the aromatic hydrocarbon feed over the catalyst in the reaction zone. It is also possible to carry out the hydroalkylation reaction under batch conditions although a batch process is less preferred because it is normally more expensive to operate and initial equipment costs are higher based upon the same size process.

Although a fixed bed reactor is mentioned above, most any type of reaction zone can be used as the particular type of reaction zne is not believed to be a critical parameter of the invention.

The reaction mixture from the reaction zone can usually be conveniently separated into the desired components by simple fractional distillation, and recycle of the unreacted feedstock and unreacted hydrogen can be accomplished as desired. The hydroalkylation products can be further purified as desired after separation from unreacted feedstock.

It is generally desirable to pretreat the catalyst with hydrogen gas prior to contacting the catalyst with the aromatic hydrocarbon in order to prereduce the catalyst. Based upon the runs described hereinafter, the hydrogen pressure and feed rate for the pretreating step generally is the same as that to be employed when contacting the aromatic hydrocarbon with the catalyst. In the hydroalkylation runs of the examples hereinafter described, the catalyst in the reactor was first reduced at 150° C. for 15 minutes under 3,450 kPa (500 psig) hydrogen at a hydrogen flow rate of 0.32 liters per minute before benzene was introduced to the reactor. Hydrogen pressure during the hydroalkylation process was maintained at 3,450 kPa (500 psig) and at a flow rate of about 0.32 liters per minute.

EXAMPLE I

Catalyst Preparation

The catalyst utilized in the runs of this Example, designated catalyst No. 1, was prepared in the following manner. A glass tube of 45 millimeter diameter, equipped with heating means and means for passing an aqueous solution of compounds therethrough, was charged with 200 grams of a type X crystalline zeolite (Davison 13 X mole sieves of 8-12 mesh manufactured by Davison Chemical Division of W. R. Grace and Co., Baltimore, Maryland). An aqueous solution of 400 grams of ammonium chloride, 100 grams of rare earth chlorides, and 200 grams of nickel chloride ($NiCl_2$) hexahydrate in 4 liters of deionized water was prepared. The rare earth chlorides were utilized as a commercially available mixture of the following composition:

$MCl_3 \cdot 6H_2O$ wherein M=lanthanum 23%, cerium 43.5%, praseodymium 5.4%, neodymium 17.9%, samarium 1.9%, gadolinium 0.6%, and others 0.2%. The crystalline zeolite material was first wetted with a portion of the above solution and then charged to the tubular glass reactor described above and the remainder of the aqueous solution pumped through the crystalline zeolite bed, the material was cooled, filtered, and washed six times with 350ml portions of water and then allowed to dry in ambient air. A portion (27.3 grams) of the cation-exchanged crystalline zeolite was then treated with a solution of 0.054 gram of chloroplatinic acid ($H_2PtCl_6$) hexahydrate in 25 ml of water under total impregnation conditions. The impregnated crystalline zeolite was dried under vacuum to give a weight of 26.2 grams of the zeolite material. This material was then calcined by heating for about 4 hours in a furnace to about 205° C. (400° F.) and then the temperature increased slowly up to about 524° C. (975° F.) over an eight hour period and then allowed to cool in the air. The catalyst thus prepared contained 0.1% platinum, 4.68% nickel, 9.5% rare earths, and 0.63% sodium by weight.

Benzene Hydroalkylation

The catalyst (No. 1) described above was utilized in the hydroalkylation of benzene in Run No. 1 described below in Table I. In these hydroalkylation runs, a small tubular reactor equipped for continuous reaction operation was charged with 10 grams (13 ml) of the catalytic material. The catalyst was prereduced at 150° C. under 3450 kPa (500 psig) hydrogen at a flow rate of 0.32 liters per minute of hydrogen for a period of 15 minutes. During each benzene hydroalkylation run, the hydrogen pressure was maintained at 3450 kPa (500 psig) and at a flow rate of 0.32 liters per minute of hydrogen. Run No. 2 of Table I was carried out after the catalyst had been regenerated according to the procedure previously described. Runs 3 and 4 of the table below were runs of the invention and were carried out after the catalyst had been modified according to the instant invention by charging 50 parts per million of carbon tetrachloride in the benzene feed over a period of four hours to provide 0.028 grams of carbon tetrachloride per 10 grams of the catalyst (2.6 milligrams [mg] of chlorine [Cl] per gram of catalyst). Other reaction conditions and the results obtained in the hydroalkylation runs are shown in Table I.

Table I

| Run No. | Regen-eration | Temp. °C. | Benzene LHSV | Benzene Conv. % | Selectivity, Wt. %[a] CH[b] | Selectivity, Wt. %[a] CHB[c] | Weight Ratio CHB/CH |
|---|---|---|---|---|---|---|---|
| 1 | No | No | 170 | 15.6 | 9.0 | 12.2 | 74.4 | 6.1 |
| 2 | No | Yes | 170 | 18.0 | 10.8 | 14.8 | 69.4 | 4.7 |
| 3 | Yes | No | 175 | 12.8 | 12.1 | 8.3 | 75.1 | 9.1 |
| 4 | Yes | No | 168 | 12.8 | 10.4 | 9.6 | 75.0 | 7.8 |

[a] Analysis by gas-liquid phase chromatography (GLC) of reaction zone effluent.
[b] CH = Cyclohexane.
[c] CHB = Cyclohexylbenzene.

A comparison of the results of control Runs 1 and 2 with invention Runs 3 and 4, particularly noting the weight ratio of CHB to CH, clearly demonstrates the improvement in selectivity to CHB without a reduction in conversion of benzene but at a lower LHSV when practicing the present invention under the conditions employed.

EXAMPLE II

The catalyst utilized in the runs of this Example (catalyst No. 2) was prepared in essentially the same manner utilized for the preparation of catalyt No. 1 of Example I above. In this instance, however, the catalyst was prepared in a much larger quantity and the particular catalyst utilized in Run No. 5 below was a used catalyst that had been effectively employed for a period of time in the hydroalkylation of benzene to cyclohexylbenzene but which had decreased significantly in activity and selectivity in the hydroalkylation process. In Run No. 6 utilizing this catalyst, the hydroalkylation procedure was carried out after performing a regeneration process on the catalyst in the manner previously described. The results obtained in Run No. 6 are also presented in Table II below. Run No. 7 is a run carried out according to the instant invention wherein the catalyst used in Run No. 6 was treated with carbon tetrachloride in the benzene feed over a three-hour period to provide 0.015 gram of carbon tetrachloride per 12.5 grams of catalyst (1.1 mg Cl per gram of catalyst).

The runs of Example II described above were carried out utilizing a reaction system for continuous operation as previously described wherein the reaction zone was charged with 15 ml (12.5 grams) of the catalyst described earlier. Other conditions utilized in the hydroalkylation runs and the results obtained are shown below in Table II.

Table II

| Run No. | Regen-eration | Temp. °C. | Benzene LHSV | Benzene Conv. % | Selectivity, Wt. % CH | Selectivity, Wt. % CHB | Weight Ratio CHB/CH |
|---|---|---|---|---|---|---|---|
| 5 | No | No | 190 | 10.0 | 1.5 | 35.8 | 58.7 | 1.6 |
| 6 | No | Yes | 169 | 20.0 | 9.1 | 9.3 | 76.4 | 8.2 |

Table II-continued

| Run No. | CCl4 | Regen- eration | Temp. °C. | Benzene LHSV | Benzene Conv. % | Selectivity, Wt. % CH | Selectivity, Wt. % CHB | Weight Ratio CHB/CH |
|---|---|---|---|---|---|---|---|---|
| 7 | Yes | Yes | 167 | 6.3 | 11.8 | 7.5 | 78.6 | 10.4 |

A comparison of the results of invention Run 7 with the results of control Runs 5 and 6 shows an increase in weight ratio of CHB to CH and an increase in selectivity to CHB without a decrease in conversion but at a lower LHSV under the conditions used when employing a catalyst and the process of the present invention.

EXAMPLE III

Catalyst No. 3 was prepared in essentially the same manner as catalyst No. 1 of Example I above with the exception that the amount of platinum compound employed in the impregnation step was sufficient to provide 0.15 weight percent platinum and a small amount of nickel chloride was also added to the catalyst in the impregnation step such that the final catalyst contained a total of 4.83 weight percent nickel in addition to 9.5 weight percent rare earths and 0.63 weight percent sodium. Run No. 8 utilizing the above catalyst is a control run wherein the fresh or unused catalyst was employed. Run No. 9 was carried out after the catalyst was regenerated in the manner previously described and Run No. 10 is a run according to the instant invention in which the regenerated catalyst was modified by the addition of 100 parts per million of carbon tetrachloride to the benzene feed over a two-hour period to provide 0.030 gram of carbon tetrachloride per 10.8 grams of catalyst (2.6 mg Cl per gram of catalyst). The results obtained in these three runs as well as other reaction conditions utilized are shown below in Table III.

Table III

| Run No. | CCl4 | Regen- eration | Temp. °C. | Benzene LHSV | Benzene Conv. % | Selectivity, Wt. % CH | Selectivity, Wt. % CHB | Weight Ratio CHB/CH |
|---|---|---|---|---|---|---|---|---|
| 8 | No | No | 160 | 17 | 10.1 | 15.2 | 73.2 | 4.8 |
| 9 | No | Yes | 173 | 20 | 11.1 | 15.3 | 73.0 | 4.8 |
| 10 | Yes | Yes | 172 | 14 | 9.8 | 7.2 | 80.6 | 11.1 |

A comparison of the results of invention Run 10 with control Runs 8 and 9 shows a substantial increase in the weight ratio of CHB/CH with only a small decrease in benzene conversion and at a lower LHSV under the conditions employed.

EXAMPLE IV

Catalyst No. 4 utilized in the runs of this Example was prepared in essentially the same manner as that described for catalyst No. 1 of Example I above. However, in this instance, the concentration of nickel chloride in the cation exchange solution was 2.5 weight percent rather than 5 weight percent as utilized for the preparation of catalyst No. 1. The catalyst (No. 4) thus prepared contained 0.10 weight percent platinum, 3.18 weight percent nickel and an estimated 10-11 weight percent rare earths and 0.7 weight percent sodium. This catalyst was utilized for the hydroalkylation of benzene under the conditions of hydrogen pressure and hydrogen flow rate previously described and the results shown for Run No. 11 were obtained with this catalyst prior to any regeneration or modification treatment according to the present invention. The results with Run No. 12 were obtained with the above catalyst after said catalyst had been regenerated. Run No. 13 was carried out according to the instant invention in which the catalyst (after Run No. 12) was treated with 100 parts per million of carbon tetrachloride in the benzene feed over a two-hour period to provide 0.020 gram of carbon tetrachloride per 10.6 grams of catalyst (1.7 mg Cl per gram of catalyst). The results obtained in Runs 11, 12, and 13 as well as other conditions employed in the hydroalkylation runs are presented below in Table IV.

Table IV

| Run No. | CCl4 | Regen- eration | Temp. °C. | Benzene LHSV | Benzene Conv. % | Selectivity, Wt. % CH | Selectivity, Wt. % CHB | Weight Ratio CHB/CH |
|---|---|---|---|---|---|---|---|---|
| 11 | No | No | 170 | 6.7 | 7.1 | 21.1 | 64.8 | 3.1 |
| 12 | No | Yes | 172 | 13.3 | 5.2 | 23.1 | 67.3 | 2.9 |
| 13 | Yes | Yes | 170 | 6.7 | 5.3 | 13.6 | 73.6 | 5.4 |

The invention run, Run 13, when compared with the control runs, Runs 11 and 12, demonstrates that practice of the present invention provides an increase in the weight ratio of CHB to CH and selectivity to CHB with some decrease in conversion to benzene and LHSV over Run 12 under the conditions employed.

EXAMPLE V

The catalyst employed in the runs of this Example was prepared in essentially the same procedure as that given for catalyst No. 1 of Example I with the exception that the concentration of nickel chloride in the cation exchange solution in this instance (catalyst No. 5) was 10 weight percent rather than 5 weight percent as in the case of catalyst No. 1. Catalyst No. 5 also contained 0.2 weight percent platinum, 6.5 weight percent nickel, 0.72 weight percent sodium and an estimated 9–10 weight percent rare earths.

Benzene hydroalkylation runs were carried out in the continuous reaction system previously described with the catalyst described above (No. 5). In Run No. 14, the catalyst was utilized prior to any regeneration or modification treatment according to the instant invention. In Run No. 15, the catalyst had been treated with 50 parts per million of carbon tetrachloride in the benzene feed over a five-hour period according to the instant invention to provide 0.033 gram of carbon tetrachloride per 11.5 grams of catalyst (2.6 mg Cl per gram of catalyst).

gram of carbon tetrachloride per 11.5 grams of catalyst (1.8 mg Cl per gram of catalyst). The results obtained in these runs as well as other reaction conditions employed are presented below in Table VI.

Table VI

| Run No. | CCl4 | Regeneration | Temp. °C. | Benzene LHSV | Benzene Conv. % | Selectivity, Wt. % CH | Selectivity, Wt. % CHB | Weight Ratio CHB/CH |
|---|---|---|---|---|---|---|---|---|
| 18 | No | No | 170 | 17 | 8.7 | 43.7 | 40.2 | 0.9 |
| 19 | No | Yes | 190 | 15 | 13.4 | 32.1 | 64.2 | 2.0 |
| 20 | Yes | Yes | 190 | 16 | 8.9 | 12.4 | 77.5 | 6.3 |
| 21 | Yes | Yes | 170 | 13 | 9.6 | 14.6 | 75.0 | 5.1 |

It should be noted that this treatment was carried out prior to any regeneration treatment of the catalyst. In Run No. 16, the catalyst (after Run No. 15) had been regenerated according to the procedure previously described and then treated with 50 parts per million of carbon tetrachloride in the benzene feed for one hour to provide 0.011 gram of carbon tetrachloride per 11.5 grams of catalyst (0.9 mg Cl per gram of catalyst). This run also is according to the instant invention. Run No. 17 is similar to Run No. 16 but under different reaction conditions. The runs of this Example were carried out using the continuous reaction system previously described under the previously described conditions of hydrogen pressure and hydrogen flow rate. The results of the runs and other reaction conditions utilized during the runs are presented below in Table V.

Comparing Runs 18 and 19, the improvement resulting from the regeneration of the catalyst is apparent, although some of the improvement may have been due to the higher reaction temperature of Run 19. Comparing Run 19, the regenerated catalyst, with invention Run 20, the improvement in the weight ratio of CHB to CH and selectivity to CHB resulting from the practice of the present invention is seen along with some reduction in conversion of the benzene feed and the LHSV. Invention Run 21 shows a substantial improvement over both control Runs 18 and 19 even though the reaction temperature is lower than that used in Run 19; however, the activity of the catalyst of Run 21 is lower.

EXAMPLE VII

Catalyst No. 7 was prepared in essentially the same

Table V

| Run No. | CCl4 | Regeneration | Temp. °C. | Benzene LHSV | Benzene Conv. % | Selectivity, Wt. % CH | Selectivity, Wt. % CHB | Weight Ratio CHB/CH |
|---|---|---|---|---|---|---|---|---|
| 14 | No | No | 164 | 16 | 8.7 | 20.8 | 60.4 | 2.9 |
| 15 | Yes | No | 170 | 15 | 6.6 | 21.2 | 62.1 | 2.9 |
| 16 | Yes | Yes | 170 | 15 | 10.6 | 9.4 | 79.2 | 8.4 |
| 17 | Yes | Yes | 165 | 16 | 8.3 | 11.1 | 78.3 | 7.0 |

In this series of runs, invention Run 15 gave substantially the same results as noninvention Run 14. Run 16 shows the improvement in results when the invention catalyst of Run 15 is regenerated.

EXAMPLE VI

Another series of runs was carried out utilizing another portion of the same catalyst employed in Example V under somewhat different reaction conditions and a different sequence of treatment steps used to produce the catalyst, catalyst No. 6.

The hydroalkylation runs of this Example were carried out in the continuous reaction system previously described and under the conditions of hydrogen pressure and hydrogen flow rate also previously described. Run No. 18 was made utilizing catalyst No. 6 prior to any regeneration or modification treatment while Run No. 19 was made after the catalyst had been regenerated according to the procedure previously described. Runs 20 and 21 were made after the catalyst had been modified according to the instant invention by the addition of 50 parts per million of carbon tetrachloride in the benzene feed for a period of 2.5 hours to provide 0.022 manner as that described for catalyst No. 5 above with the exception that the amount of the platinum compound utilized in the impregnation step was essentially one-half of that provided for catalyst No. 5. Thus, catalyst, No. 7 contained 0.1 weight percent platinum, 6.5 weight percent nickel, 0.72 weight percent sodium and an estimated 9-10 weight percent rare earths.

Catalyst No. 7 was utilized in benzene hydroalkylation runs under the same conditions of hydrogen pressure and flow rate previously described and with the same continuous reaction system. Run No. 22 was carried out without any catalyst treatment such as regeneration or modification with a chlorine- or bromine-containing compound according to the instant invention. Run No. 23 was carried out after the catalyst had received the treatment procedure of the instant invention wherein 50 parts per million of carbon tetrachloride in the benzene feed was added over a period of 3.5 hours to provide 0.024 grams of carbon tetrachloride per 11.3 grams of catalyst (2.0 mg Cl per gram of catalyst). Thus, neither catalyst 22 or 23 had been regenerated. The results obtained in the above runs and other reaction conditions utilized are presented in Table VII below.

Table VII

| Run No. | CCl4 | Regeneration | Temp. °C. | Benzene LHSV | Benzene Conv. % | Selectivity, Wt. % CH | Selectivity, Wt. % CHB | Weight Ratio CHB/CH |
|---|---|---|---|---|---|---|---|---|
| 22 | No | No | 160 | 20 | 7.8 | 19.2 | 69.2 | 3.6 |

Table VII-continued

| Run No. | CCl4 | Regeneration | Temp. °C. | Benzene LHSV | Conv. % | Selectivity, Wt. % CH | CHB | Weight Ratio CHB/CH |
|---|---|---|---|---|---|---|---|---|
| 23 | Yes | No | 160 | 14.7 | 10.8 | 14.8 | 71.3 | 4.8 |

The results of the invention Run 23 when compared with those of control Run 22 demonstrate the improvement resulting from the present invention. The LHSV of benzene in the invention run was lower but the percent conversion of benzene was higher.

EXAMPLE VIII

Catalyst No. 8 utilized in the runs of this Example was prepared to contain nickel, rare earths and platinum on an acidic crystalline zeolite of type X and also contained a small amount of ruthenium as an added catalyst component. This catalyst was prepared by cation exchanging 250 grams of a type X crystalline zeolite (Davison 13X molecular sieves) with a solution of 400 grams of ammonium chloride, 100 grams of rare earth chlorides and 400 grams of nickel chloride hexahydrate in 4 liters of water in a manner essentially the same as that described above in Example I. The cation-exchanged zeolite was filtered and washed and allowed to dry in air as described earlier. About one-half of the cation-exchanged zeolite was calcined under conditions essentially the same as those described in Example I to provide a support material which contained 6.5% nickel and 0.72% sodium. A portion (41.2 grams) of the uncalcined cation-exchanged material was impregnated with a solution of 0.08 gram of chloroplatinic acid hexahydrate and 0.081 gram of ruthenium trichloride in 50 ml of distilled water. The water was evaporated to dryness on a rotary evaporator. The impregnated support was then calcined by heating to about 204° C. (400° F.) overnight and then increasing the temperature to about 518° C. (965° F.) over an eight-hour period. The calcined catalyst was allowed to cool in ambient air and was then ready for utilization in benzene hydroalkylation runs. The final catalyst thus contained 0.1% platinum, 0.1% ruthenium, 6.5% nickel, 0.72% sodium and an estimated 9–10% rare earths by weight.

Run No. 24 utilizing the above-described catalyst was carried out without any modification of the catalyst such as by regeneration or addition of a halide-containing compound according to the instant invention. Run No. 25 was carried out after the catalyst had been treated with 50 parts per million of carbon tetrachloride in the benzene feed for a period of 2.5 hours to provide about 0.025 grams of carbon tetrachloride per 11.2 grams of catalyst (2.0 mg Cl per gram of catalyst). Run No. 26 was carried out after the catalyst utilized in Run No. 25 had been regenerated under typical conditions described earlier and then again treated with 50 parts per million of carbon tetrachloride in the benzene feed for 1.5 hours to provide about 0.015 gram of carbon tetrachloride per 11.2 grams of catalyst (1.2 mg Cl per gram of catalyst). The hydroalkylation runs were carried out under the previously described conditions of hydrogen pressure and flow rate. The results are described in Table VIII.

Table VIII

| Run No. | CCl4 | Regeneration | Temp. °C. | Benzene LHSV | Conv. % | Selectivity, Wt. % CH | CHB | Weight Ratio CHB/CH |
|---|---|---|---|---|---|---|---|---|
| 24 | No | No | 175 | 18 | 6.6 | 53.0 | 43.9 | 0.8 |
| 25 | Yes | No | 175 | 18 | 8.2 | 42.7 | 53.6 | 1.3 |
| 26 | Yes | Yes | 175 | 6.7 | 8.6 | 15.1 | 72.1 | 4.7 |

A comparison of control Run 24 with invention Run 25 shows an improvement in the results due to treatment of the catalyst of Run 25 accordance with the invention, but since neither catalyst was regenerated the weight ratio of CHB to CH and selectivity to CHB was rather low. A comparison of invention Run 25 with invention Run 26 employing the regenerated catalyst of Run 25 but at approximately ⅓ the LHSV of Run 25 shows the substantial improvement brought about by regeneration of the catalyst under the conditions employed. The addition of ruthenium to the catalysts of Runs 24, 25 and 26 does not appear to promote the desired reaction under the conditions employed.

EXAMPLE IX

Catalyst No. 9 was prepared in a manner similar to that utilized for the preparation of catalyst No. 1 of Example I with the exception that in the cation exchange step the mixture of rare earth compounds was replaced by a single rare earth compound. In this instance, cerous chloride ($CeCl_3$) was utilized in the cation exchange step. In the preparation of this catalyst, 200 grams of a type X crystalline zeolite (Davison 13X mole sieves) was wetted with a portion of a solution of 400 grams of ammonium chloride, 200 grams of nickel chloride hexahydrate and 100 grams of cerous chloride in 4 liters of deionized water. The crystalline zeolite material was then charged to the cation exchange reactor previously employed and the remainder of the above-described solution pumped over the zeolite bed at a temperature of about 100° C. and at about 0.25 LHSV. The material was cooled, filtered and washed six times with 350 ml portions of water and then permitted to dry in ambient air. A portion (60 grams) of the cation-exchanged crystalline zeolite was impregnated with a solution of 0.0966 grams of chloroplatinic acid hexahydrate in about 50 ml of absolute ethanol. The ethanol was removed under reduced pressure and additional ethanol added and then removed as before. The catalyst was calcined under conditions similar to those previously employed, that is, heating up to about 205° C. (401° F.) and holding at this temperature overnight followed by heating over an eight-hour period up to about 524° C. (975° F.) This catalyst (No. 9) contained 0.091 weight percent platinum and an estimated 4–5 weight percent nickel, 9–10 weight percent cerium and 0.6 weight percent sodium.

Run No. 27 was a benzene hydroalkylation run using the above-described catalyst prior to any treatment such as regeneration or modification by addition of a halide-containing compound according to the instant invention. Run No. 28 was carried out by treating the catalyst according to the instant invention with 50 parts per million of carbon tetrachloride in the benzene feed for a period of 3 hours to provide 0.020 g carbon tetrachloride per 11.3 grams of catalyst (1.6 mg Cl per gram of catalyst). Run No. 29 was carried out following regeneration of the catalyst used in Run No. 28 under conditions previously described but without retreating the catalyst with CCl₄ subsequent to regeneration. Run No. 30 was carried out by treating the regenerated catalyst according to the instant invention with 100 parts per million of carbon tetrachloride in the benzene feed for a period of 2.5 hours to provide 0.041 gram of carbon tetrachloride per 11.3 grams of catalyst (3.3 mg Cl per gram of catalyst). These benzene hydroalkylation runs were carried out under the conditions of hydrogen pressure and flow rate previously described. The results obtained in Runs 27–30 and other conditions employed in the hydroalkylation runs are presented in Table IX below.

Table IX

| Run No. | CCl₄ | Regen-eration | Temp. °C. | Benzene LHSV | Conv. % | Selectivity, Wt. % CH | CHB | Weight Ratio CHB/CH |
|---|---|---|---|---|---|---|---|---|
| 27 | No | No | 203 | 20 | 12.2 | 51.6 | 45.9 | 0.9 |
| 28 | Yes | No | 158 | 6.7 | 13.8 | 29.7 | 67.6 | 2.3 |
| 29 | No[a] | Yes | 184 | 14 | 12.1 | 31.6 | 65.7 | 2.1 |
| 30 | Yes | Yes | 173 | 14 | 8.8 | 14.5 | 76.6 | 5.3 |

[a]The catalyst was not retreated with CCl₄ after regeneration.

The results shown in Table IX show the improvement in the results when employing the present invention whether a mixture of rare earths is used as in the previous runs or a single rare earth, cerium, is used as in invention Runs 28–30.

EXAMPLE X

Catalyst No. 10 utilized in the runs of this Example was prepared in essentially the same manner as that described for catalyst No. 9 above with the exception that the cerous chloride was replaced by lanthanum chloride (LaCl₂) hexahydrate in the cation exchange step. A portion (50 grams) of the cation-exchanged crystalline zeolite was impregnated with a solution of 0.095 gram of chloroplatinic acid hexahydrate in about 50 ml of absolute ethanol. The ethanol was removed under reduced pressure, more ethanol added and then removed as before. The recovered material was heated under calcination conditions similar to those previously employed in the preparation of catalyst No. 9. The catalyst contained 0.1% platinum and an estimated 4–5% nickel, 9–10% lanthanum and 0.6% sodium by weight.

Catalyst No. 10 was employed in Run No. 31 for hydroalkylation of benzene prior to any treatment of the catalyst by regeneration or modification by addition of halide-containing compounds according to the instant invention. Run No. 32 was carried out after the catalyst (No. 10) had been regenerated under conditions previously described. Run No. 33, a run according to the instant invention, was carried out after the regenerated catalyst had been modified by treatment with 100 parts per million of carbon tetrachloride in the benzene feed added over a 4.0 hour period to provide 0.055 gram of carbon tetrachloride per 11.1 grams of catalyst (4.5 mg Cl per gram of catalyst). These hydroalkylation runs were carried out under the previously employed conditions of hydrogen pressure and hydrogen flow rate. Results obtained in Runs 31–33 are shown below in Table X along with other reaction conditions employed in said runs.

Table X

| Run No. | CCl₄ | Regen-eration | Temp. °C. | Benzene LHSV | Conv. % | Selectivity, Wt. % CH | CHB | Weight Ratio CHB/CH |
|---|---|---|---|---|---|---|---|---|
| 31 | No | No | 159 | 20 | 7.5 | 31.7 | 67.6 | 2.1 |
| 32 | No | Yes | 185 | 23 | 13.6 | 21.1 | 68.2 | 3.2 |
| 33 | Yes | Yes | 179 | 16 | 6.9 | 14.2 | 76.1 | 5.3 |

Invention Run 33 as compared to control Runs 31 and 32 illustrates that practice of the present invention produces an improvement in weight ratio of CHB to CH and in selectivity to CHB at a somewhat lower LHSV and conversion of benzene. Run 33 also demonstrates that the rare earth lanthanum can be employed in carrying out the present invention.

EXAMPLE XI

Catalyst No. 11 utilized in the runs of this Example was prepared in essentially the same manner as that described for catalyst Nos. 1 and 2 of Examples I and II, respectively, with the exception that the chloroplatinic acid was impregnated after the calcination step. Thus, the amount of platinum, nickel, and rare earths on the final hydroalkylation catalyst was essentially the same as those shown for the above-mentioned catalyst Nos. 1 and 2.

In Run No. 34 utilizing catalyst No. 11, the hydroalkylation run was carried out with the catalyst prior to any regeneration or modification treatment according to the instant invention. Run No. 35 was carried out after the catalyst had been modified by the addition of 50 parts per million of carbon tetrachloride in the benzene feed for a three-hour period to provide 0.026 gram of carbon tetrachloride per 11.0 grams of catalyst (2.2 mg Cl per gram of catalyst). Run No. 36 was also carried out after the above modification described for the catalyst employed in Run No. 35 but under slightly different reaction conditions. These hydroalkylation runs were carried out under the same hydrogen pressure and flow rate and in the same continuous reaction system as that previously utilized in the Examples above. The results obtained in these hydroalkylation runs as well as the other reaction conditions utilized are presented below in Table XI.

Table XI

| Run No. | CCl4 | Regen- eration | Temp. °C. | Benzene LHSV | Benzene Conv. % | Selectivity, Wt. % CH | Selectivity, Wt. % CHB | Weight Ratio CHB/CH |
|---|---|---|---|---|---|---|---|---|
| 34 | No | No | 185 | 21.5 | 12.8 | 21.6 | 67.3 | 3.1 |
| 35 | Yes | No | 185 | 19.0 | 10.5 | 11.4 | 73.3 | 6.4 |
| 36 | Yes | No | 175 | 18.8 | 8.6 | 12.1 | 73.2 | 6.1 |

Comparison of control Run 34 with invention Run 35 demonstrates an improved result in the weight ratio of CHB to CH and in selectivity to CHB, although the invention catalyst was somewhat less active. The different reaction conditions of Run 36 appeared to reduce the catalyst's activity a little as compared to Run 35.

EXAMPLE XII

The catalyst employed in the hydroalkylation runs of this Example was a portion of the same catalyst utilized for the runs of Example XI above. The hydroalkylation runs were carried out under the same conditions of hydrogen pressure and flow rate and in the same type of continuous reaction system previously employed. Run No. 37 was carried out prior to the treatment of the catalyst in a regeneration procedure or by addition of a halogen-containing compound to modify the catalyst according to the instant invention. Thus, Run No. 37 is similar to Run No. 34 of Example XI except that the reaction conditions were different. Run No. 38 was carried out after the catalyst utilized in Run No. 37 was regenerated according to the typical procedure previously described. Run No. 39 was carried out after the regenerated catalyst had been modified by the addition of 50 parts per million of carbon tetrachloride in the benzene feed over a period of 5.5 hours which provided 0.0325 gram of carbon tetrachloride per 12.5 grams of catalyst (2.3 mg Cl per gram of catalyst). The results of these hydroalkylation runs as well as other reaction conditions employed are presented in Table XII.

Table XII

| Run No. | CCl4 | Regen- eration | Temp. °C. | Benzene LHSV | Benzene Conv. % | Selectivity, Wt. % CH | Selectivity, Wt. % CHB | Weight Ratio CHB/CH |
|---|---|---|---|---|---|---|---|---|
| 37 | No | No | 170 | 13.3 | 10.8 | 44.4 | 52.8 | 1.2 |
| 38 | No | Yes | 170 | 18.0 | 15.6 | 26.7 | 64.7 | 2.4 |
| 39 | Yes | Yes | 175 | 12.0 | 10.2 | 7.0 | 81.4 | 11.7 |

A comparison of control Run 38 with 37 shows that regeneration improves the catalyst; however, comparing these runs with invention Run 39 shows that the invention catalyst provided a substantial improvement in weight ratio of CHB to CH and selectivity to CHB but with a reduction in activity.

In summary, the results shown in Tables I–XII above demonstrate that a hydroalkylation catalyst comprising platinum, nickel, rare earths on acidic mole sieves modified by the addition of a halogen-containing compound provides an improvement in selectivity of the benzene hydroalkylation process for cyclohexylbenzene. This improvement in selectivity is seen to be achieved before or after the hydroalkylation catalyst has undergone a regeneration process involving a burn-off of coke or other carbonaceous deposits from the catalysts. Generally speaking, the improvement in selectivity for cyclohexylbenzene is accompanied by a decrease in catalyst activity as seen by reduced benzene conversions or reduced flow rate of benzene feed through the reaction zone (LHSV).

What is claimed is:

1. A composition comprising:
   at least one platinum compound supported on a calcined, acidic, nickel and rare earth-treated crystalline zeolite which additionally has a halide content ranging from about 0.5 to about 10 milligrams of elemental halogen per gram of said composition,
   wherein the rare earth content of the calcined, acidic, nickel and rare earth-treated crystalline zeolite is in the range of from about 2 to about 25 percent by weight of said composition; and
   wherein the nickel content of the calcined, acidic nickel and rare earth-treated crystalline zeolite is in a range of from about 0.01 to about 15 percent by weight of said composition.

2. The composition of claim 1 wherein the platinum content ranges from about 0.01 to about 1 percent by weight of said composition.

3. The composition of claim 1 wherein the platinum content ranges from about 0.05 to about 0.25 percent by weight of said composition.

4. The composition of claim 1 wherein the crystalline zeolite is selected from the group consisting of Type X and Type Y zeolites;
   wherein the rare earth and nickel compounds employed to treat the zeolite are selected from the group consisting of nitrates, bromides, acetates, chlorides, iodides, sulfates and mixtures thereof;
   wherein the rare earth metal is selected from the group consisting of cerium, lanthanum, praseodymium, neodymium, samarium, europium, gadolinium, terbium, dysprosium, holmium, erbium, thulium, ytterbium, lutetium and mixtures thereof;
   wherein the platinum compound is selected from the group consisting of ammonium hexachloroplatinate(IV), ammonium tetrachloroplatinate(II), chloroplatinic acid, diaminoplatinum dinitrite, platinic acid, platinum tetrachloride and mixtures thereof;
   wherein the halide source is selected from the group consisting of fluorine, bromine, chlorine, iodine, carbon tetrachloride, carbon tetraiodide, tetrachloroethylene, chloroform, bromoform, dichloromethane, dibromomethane, difluoromethane, chloromethane, bromomethane, 1,4-dichlorobutane, 1,4-dibromobutane, 1-chlorobutane, 1-fluorobutane, 1-bromobutane, 1,2-dichloroethane, 1,2-dibromoethane, 2-chloropropane, 2-bromopropane, acetyl iodide, acetyl chloride, acetyl bromide, bromochloromethane, 1-bromo-4-chlorobutane, 1,2-dichloroethylene, 1,2-dibromoethylene and mixtures thereof.

5. The composition of claim 1 wherein the crystalline zeolite is the alkali metal form with the alkali metal content of the calcined, acidic, nickel and rare earth-treated crystalline zeolite in the range of from about 0.01 to about 2 percent by weight of said composition; and wherein the halogen is chlorine or bromine.

6. The composition of claim 3 wherein the crystalline zeolite is the alkali metal form with the alkali metal content of the calcined, acidic, nickel and rare earth-treated crystalline zeolite ranges from about 0.05 to about 1 percent by weight of said composition;

wherein the rare earth content of the calcined, acidic, nickel and rare earth-treated crystalline zeolite ranges from about 5 to about 20 percent by weight of said composition;

wherein the nickel content of calcined, acidic, nickel and rare earth-treated crystalline zeolite ranges from about 1 to about 8 percent by weight of said composition; and wherein the halogen is chlorine or bromine.

7. The composition of claim 4 wherein the crystalline zeolite is selected from the group consisting of Type X and Type Y zeolites; and the platinum compound is chloroplatinic acid, the nickel compound used to treat the crystalline zeolite is nickel chloride hexahydrate, the rare earth metal compound used to treat the crystalline zeolite is a mixture of the chlorides consisting of lanthanum, cerium, praseodymium, neodymium, samarium and gadolinium, and the halide is chloride.

8. A method for the preparation of a composition comprising:

contacting a crystalline zeolite with an aqueous cation exchange solution comprising rare earth, nickel, and ammonium compounds;

removing the cation exchanged zeolite from said solution and washing said zeolite with water to remove excess ions;

calcining said cation exchanged zeolite;

cooling said calcined zeolite;

impregnating said cation exchanged zeolite with a solution comprising at least one platinum compound in a suitable solvent;

removing said solvent by evaporation;

wherein said cation exchanged zeolite is calcined and then cooled either before or after said platinum compound is impregnated on said zeolite; and contacting said platinum impregnated and calcined crystalline zeolite with a halogen-containing compound in an amount sufficient to deposit from about 0.5 to about 10 milligrams of element halogen per gram of said composition.

9. The method of claim 8 wherein said zeolite is selected from the group consisting of alkali metal Type X and Type Y zeolites;

wherein the rare earth and nickel compounds employed to treat the zeolite are selected from the group consisting of nitrates, bromides, acetates, chlorides, iodides, sulfates and mixtures thereof;

wherein the rare earth metal is selected from the group consisting of cerium, lanthanum, praseodymium, neodymium, samarium, europium, gadolinium, terbium, dysprosium, holmium, erbium, thulium, ytterbium, lutetium, and mixtures thereof;

wherein the platinum compound is selected from the group consisting of ammonium hexachloroplatinate(IV), ammonium tetrachloroplatinate(II), chloroplatinic acid, diaminoplatinum dinitrite, platinic acid, platinum tetrachloride and mixtures thereof;

wherein the halide is selected from the group consisting of fluorine, bromine, chlorine and iodine;

wherein the halide compound is selected from the group consisting of carbon tetrachloride, carbon tetraiodide, tetrachloroethylene, chloroform, bromoform, dichloromethane, dibromomethane, difluoromethane, chloromethane, bromomethane, 1,4-dichlorobutane, 1,4-dibromobutane, 1-chlorobutane, 1-fluorobutane, 1-bromobutane, 1,2-dichloroethane, 1,2-dibromomethane, 2-chloropropane, 2-bromopropane, acetyl iodide, acetyl chloride, acetyl bromide, bromochloromethane, 1-bromo-4-chlorobutane, 1,2-dichloroethylene, 1,2-dibromoethylene and mixtures thereof;

wherein the weight ratio of ammonium compound to rare earth and nickel compounds ranges from about 0.05:1 to about 20:1;

wherein said aqueous cation exchange nickel, rare earth and ammonium compound solution is contacted with said zeolite at a liquid hourly space velocity ranging from about 0.1 to about 0.5; and wherein after said zeolite is washed with water and prior to said calcination step, said zeolite is heated to a temperature ranging from about 100° to 300° C. to remove excess water and then the temperature is slowly raised to a temperature ranging from about 200° to 550° C. in order to calcine said zeolite and convert the ammonium cations to the hydrogen form.

10. The method of claim 9 wherein said composition is treated with hydrogen subsequent to the removal by evaporation of the platinum compound solvent.

11. The method of claim 8 wherein the crystalline zeolite is selected from the group consisting of Type X and Type Y zeolites; and the platinum compound is chloroplatinic acid, the nickel compound used to treat the crystalline zeolite is nickel chloride hexahydrate, the rare earth metal compound used to treat the crystalline zeolite is a mixture of the chlorides consisting of lanthanum, cerium, praseodymium, neodymium, samarium and gadolinium, and the halide is chlorine.

12. The method of claim 8 wherein the platinum content of the impregnating solution is sufficient to provide a platinum content of the cation exchanged zeolite ranging from about 0.01 to about 1 percent by weight of said composition.

13. The method of claim 8 wherein the platinum content of the impregnating solution is sufficient to provide a platinum content of the cation exchanged zeolite ranging from about 0.05 to about 0.25 percent by weight of said composition.

14. The method of claim 8 wherein the platinum impregnated and calcined crystalline zeolite is contacted with a mixture of an aromatic hydrocarbon and the halide-containing compound.

15. The method of claim 12 wherein the crystalline zeolite is the alkali metal form with the alkali metal content of the calcined, acidic, nickel and rare earth-treated crystalline zeolite in the range of from about 0.01 to about 2 percent by weight of said composition;
    wherein the rare earth content of the calcined acidic, nickel and rare earth-treated crystalline zeolite ranges from about 2 to about 25 percent by weight of said composition;
    wherein the nickel content of the calcined, acidic, nickel and rare earth-treated crystalline zeolite ranges from about 0.01 to about 15 percent by weight of said composition; and wherein the halide is chlorine or bromine.

16. The method of claim 13 wherein the crystalline zeolite is the alkali metal form with the alkali metal content of the calcined, acidic, nickel and rare earth-treated crystalline zeolite in the range of from about 0.05 to about 1 percent by weight of said composition;
    wherein the rare earth content of the calcined, acidic, rare earth-treated crystalline zeolite ranges from about 5 to about 20 percent by weight of said composition;
    wherein the nickel content of the calcined, acidic, nickel and rare earth-treated crystalline zeolite ranges from about 1 to about 8 percent by weight of said composition; and
    wherein the halide is chlorine or bromine.

* * * * *